US005696111A

United States Patent [19]
Baldwin et al.

[11] Patent Number: 5,696,111
[45] Date of Patent: Dec. 9, 1997

[54] 3-ACYLAMINOBENZAZEPINES

[75] Inventors: John J. Baldwin, Gwynedd Valley; David A. Claremon, Maple Glen; Nigel Liverton, Harleysville; Harold G. Selnick, Ambler, all of Pa.

[73] Assignee: Merck & Co., Inc., Rahway, N.J.

[21] Appl. No.: 646,368

[22] PCT Filed: Nov. 21, 1994

[86] PCT No.: PCT/US94/13413

§ 371 Date: May 16, 1996

§ 102(e) Date: May 16, 1996

[87] PCT Pub. No.: WO95/14671

PCT Pub. Date: Jun. 1, 1995

[51] Int. Cl.$^6$ ................................................ A01N 43/46
[52] U.S. Cl. ........................ 514/213; 514/214; 540/521; 540/522; 540/523
[58] Field of Search ........................ 540/521, 522, 540/523; 514/214, 213

[56] References Cited

U.S. PATENT DOCUMENTS

| | | |
|---|---|---|
| 4,470,988 | 9/1984 | Watthey . |
| 4,473,575 | 9/1984 | Watthey . |
| 4,503,060 | 3/1985 | Walther et al. . |
| 4,507,313 | 3/1985 | Braestrup et al. . |
| 4,537,885 | 8/1985 | Watthey . |
| 4,600,534 | 7/1986 | Bach et al. . |
| 4,692,522 | 9/1987 | Parsons et al. . |
| 4,775,671 | 10/1988 | Hunkeler et al. . |
| 4,820,834 | 4/1989 | Evans et al. . |
| 4,847,248 | 7/1989 | Freidinger et al. . |
| 5,044,741 | 9/1991 | Evans et al. . |
| 5,055,464 | 10/1991 | Murakami et al. . |
| 5,155,151 | 10/1992 | Freidinger et al. . |
| 5,206,234 | 4/1993 | Bock et al. . |
| 5,338,861 | 8/1994 | Botta et al. . |

FOREIGN PATENT DOCUMENTS

| | | |
|---|---|---|
| 1 190 708 | 7/1985 | Canada . |
| 0 107 095 | 5/1984 | European Pat. Off. . |
| 0 538 945 A1 | 4/1993 | European Pat. Off. . |
| 0 566 175 A2 | 10/1993 | European Pat. Off. . |
| 93/14058 | 1/1993 | Japan . |
| 9315059 | 8/1993 | WIPO . |

OTHER PUBLICATIONS

J. Gen. Physiol., vol. 96, Jul. 1990, pp. 195–215, by M.C. Sanguinetti, et al.

J. Cardiovascular Pharmacology, vol. 20 (Suppl. 2), pp. S17–S22 (1992), by L. M. Hondeghem.

*Primary Examiner*—Mukund J. Shah
*Assistant Examiner*—Michael Bucknum
*Attorney, Agent, or Firm*—Elliott Korsen; Mark R. Daniel; Francis P. Bigley

[57] ABSTRACT

This invention is concerned with novel compounds represented by structural formula I and II.

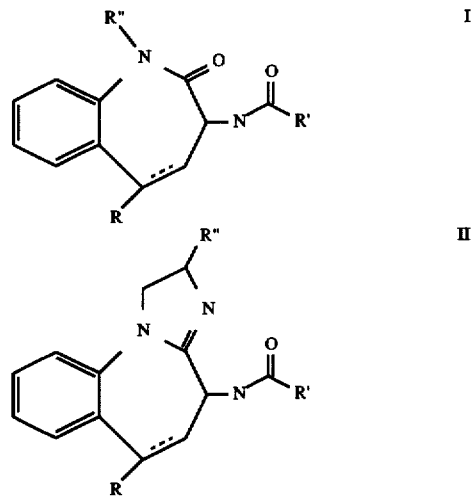

which are antiarrhythmic agents.

8 Claims, No Drawings

3-ACYLAMINOBENZAZEPINES

BACKGROUND OF THE INVENTION

Arrthythrmias often occur as complications to cardiac diseases such as myocardial infarction and heart failure. In a serious case, arrhythmias give rise to a ventricular fibrillation and can cause sudden death.

Though various antiarrythmic agents are now available on the market, those having both satisfactory effects and high safety, have not been obtained. For example, antiarrythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formulae I and II.

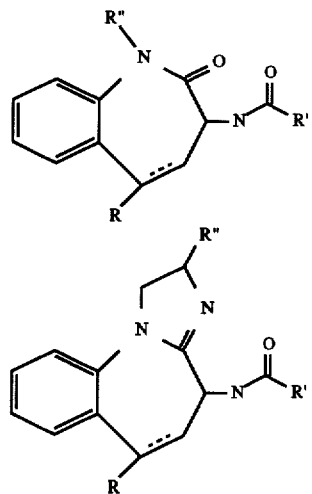

Where R is a straight or branched alkyl of $C_1$ to $C_6$, arylalkyl, aryl, heteroaryl, O-alkyl, O-acyl, carboxylic acid, aldehyde, ketone, ester;, R' is a straight or branched alkyl of $C_1$ to $C_6$, arylalkyl, aryl, N-alkyl, N-aryl, O-alkyl, or O-aryl and R" is a straight or branched alkyl or aryl group or pharmaceutically acceptable salts, hydrates and crystal forms thereof, which are useful as antiarrhythmic agents. The invention is also concerned with pharmaceutical formulations comprising one of the novel compounds as an active ingredient.

The invention is also concerned with a method of treating arrhythmia by the administration of one of the novel compounds or formulation thereof to a patient in need of such treatment.

DETAILED DESCRIPTION OF THE INVENTION

The novel compounds of this invention have structural formulae of I or II

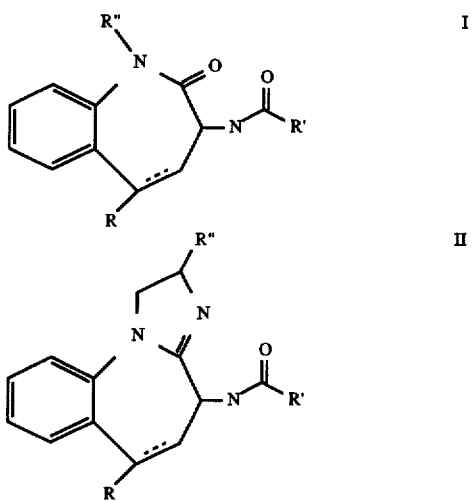

Where R is a straight or branched alkyl of $C_1$ to $C_6$, arylalkyl, aryl, heteroaryl, O-alkyl, O-acyl, carboxylic acid, aldehyde, ketone, ester;, R' is a straight or branched alkyl of $C_1$ to $C_6$, arylalkyl, aryl, N-alkyl, N-O-alkyl, O-aryl: and R" is a straight or branched Alkyl.

The pharmaceutically acceptable salts, crystal forms and hydrates of the compounds of Formula I include the conventional non-toxic salts or the quaternary ammonium salts of the compounds of Formulae I and II formed, e.g., from non-toxic inorganic or organic acids. For example, such conventional non-toxic salts include those derived from inorganic acids such as hydrochloric, hydrobromic, sulfuric, sulfuric, phosphoric, nitric and the like: and the salts prepared from organic acids such as acetic, propionic, succinic, glucolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I and H which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

One embodiment of the novel compounds of this invention is that in which the 2,3,4,5-tetrahydrobenzo[b]azepin is utilized.

Representative of the compounds within this embodiment are those depicted in Table. I.

TABLE I

| R | R' | R" | R'" |
|---|---|---|---|
| =O | 2,4-dichlorophenylpropyl | —CH₃ | —H |
| methyl carbonate (—O-Me-C(=O)—) | 2,4-dichlorophenylpropyl | —CH₃ | —H |
| benzoate (PhC(=O)O—) | 2,4-dichlorophenylpropyl | —CH₃ | —H |
| =O | 2,4-dichlorophenylpropyl | isobutyl | —H |
| phenyl | cyclohexylpropyl | —CH₃ | —H |
| phenyl (cis) | cyclohexylpropyl | —CH₃ | —H |
| phenyl (trans) | cyclohexylpropyl | —CH₃ | —H |

A second embodiment of the novel compounds of this invention is that wherein the 2,3-dihydrobenzo[b]azepin is utilized.

Representative of this embodiment are the compounds depicted in Table II.

TABLE II

| R | R' | R" |
|---|---|---|
| phenyl | 2,4-dichlorophenylpropyl | —CH₃ |
| —C≡N | 2,4-dichlorophenylpropyl | —CH₃ |
| —H | 2,4-dichlorophenylpropyl | isobutyl |
| 2-methoxyphenyl | 2,4-dichlorophenylpropyl | —CH₃ |
| 3-furyl | 2,4-dichlorophenylpropyl | —CH₃ |
| 2-furyl | 2,4-dichlorophenylpropyl | —CH₃ |
| N-methylpyrrolidinyl | 2,4-dichlorophenylpropyl | —CH₃ |
| isopropenyl | 2,4-dichlorophenylpropyl | —CH₃ |
| 3-methyl-2,3-dihydrobenzothiophen-2-yl | 2,4-dichlorophenylpropyl | —CH₃ |

TABLE II-continued

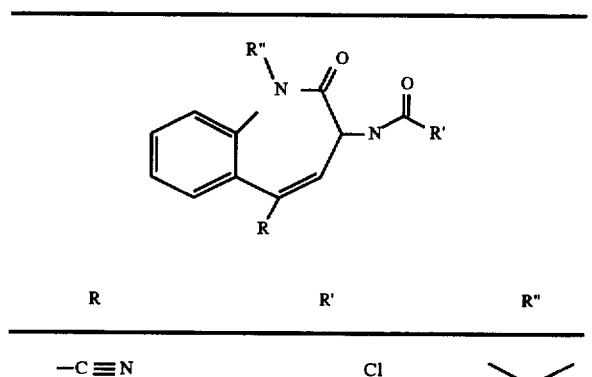

| R | R' | R" |
|---|----|----|
| —C≡N | (2,4-dichlorophenyl)propyl | i-Pr |

A third embodiment of the novel compounds of this invention is that wherein an imidazoline ring is appended at the 1,2 position of the benzazepine. Specific compounds within this embodiment are those depicted in Table III.

TABLE III

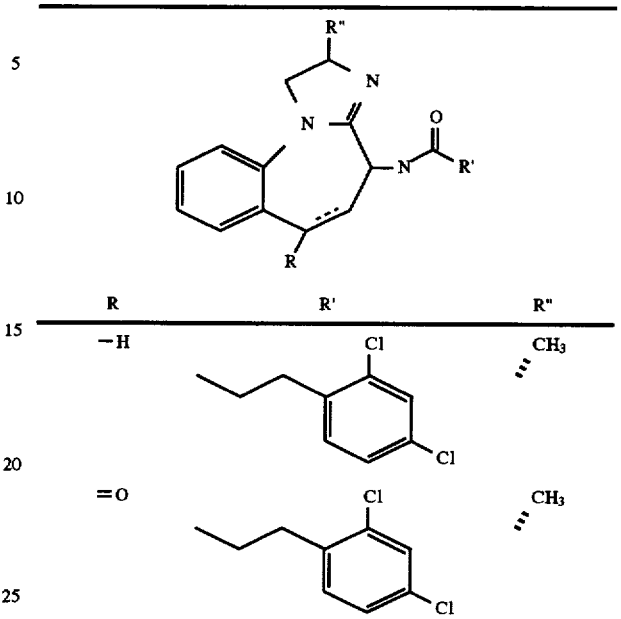

| R | R' | R" |
|---|----|----|
| —H | (2,4-dichlorophenyl)propyl | CH₃ |
| =O | (2,4-dichlorophenyl)propyl | CH₃ |

A novel process for preparing the compounds of this invention is schematically exemplified below in schemes 1 to 5, and these steps are well known in the art and/or described in the Examples that follow.

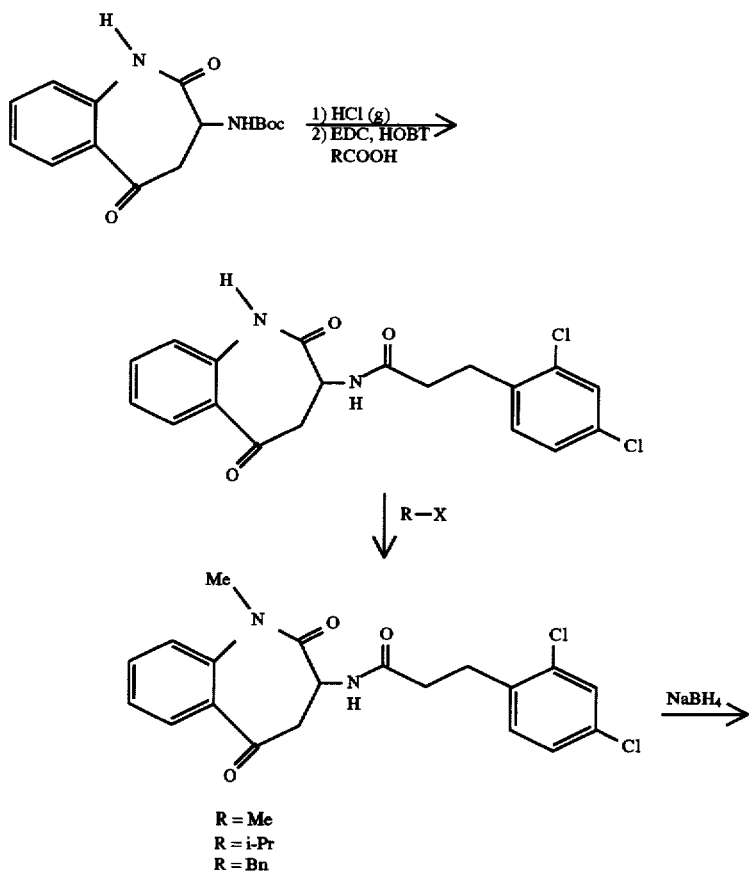

R = Me
R = i-Pr
R = Bn

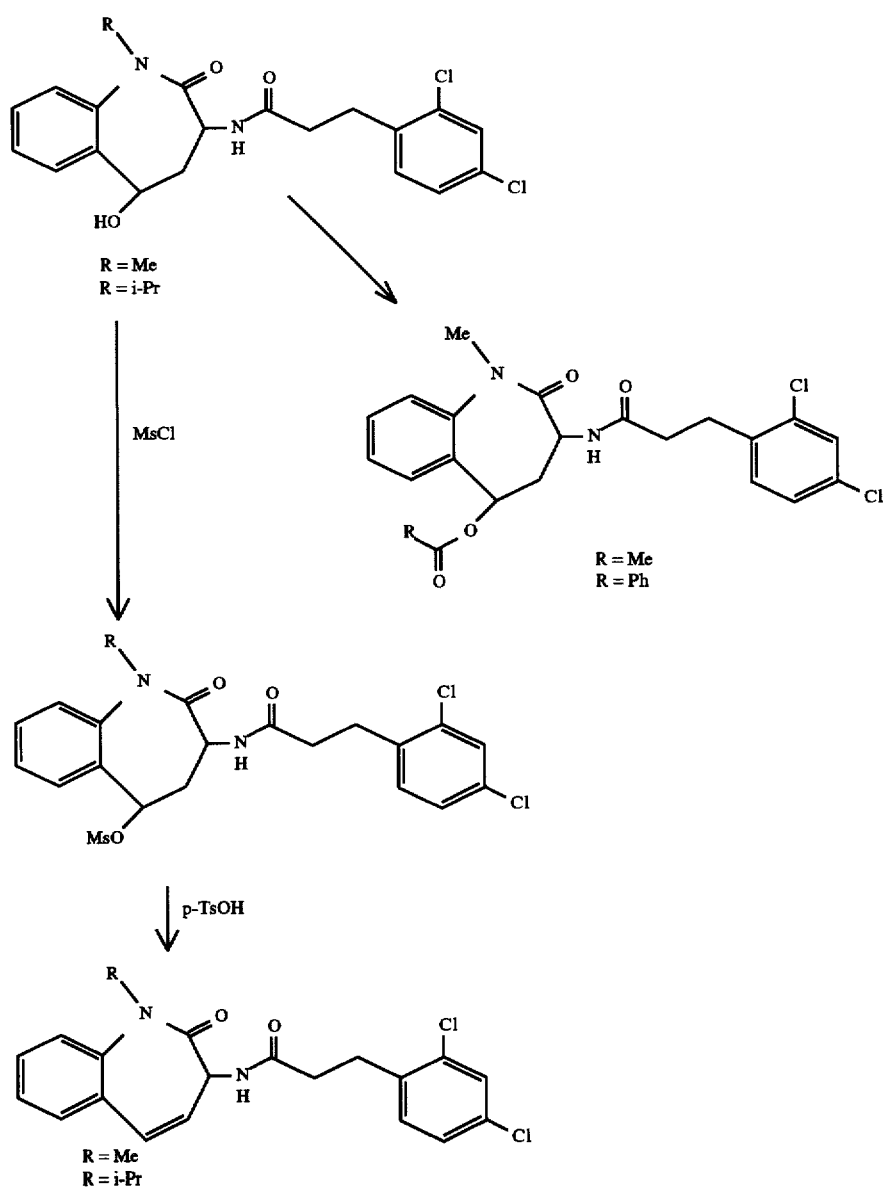
SCHEME I
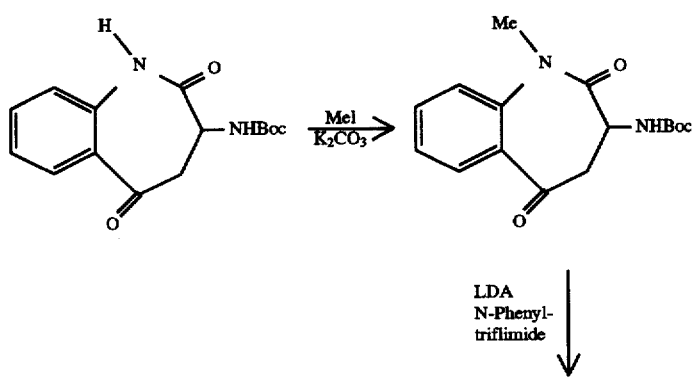

-continued
SCHEME I
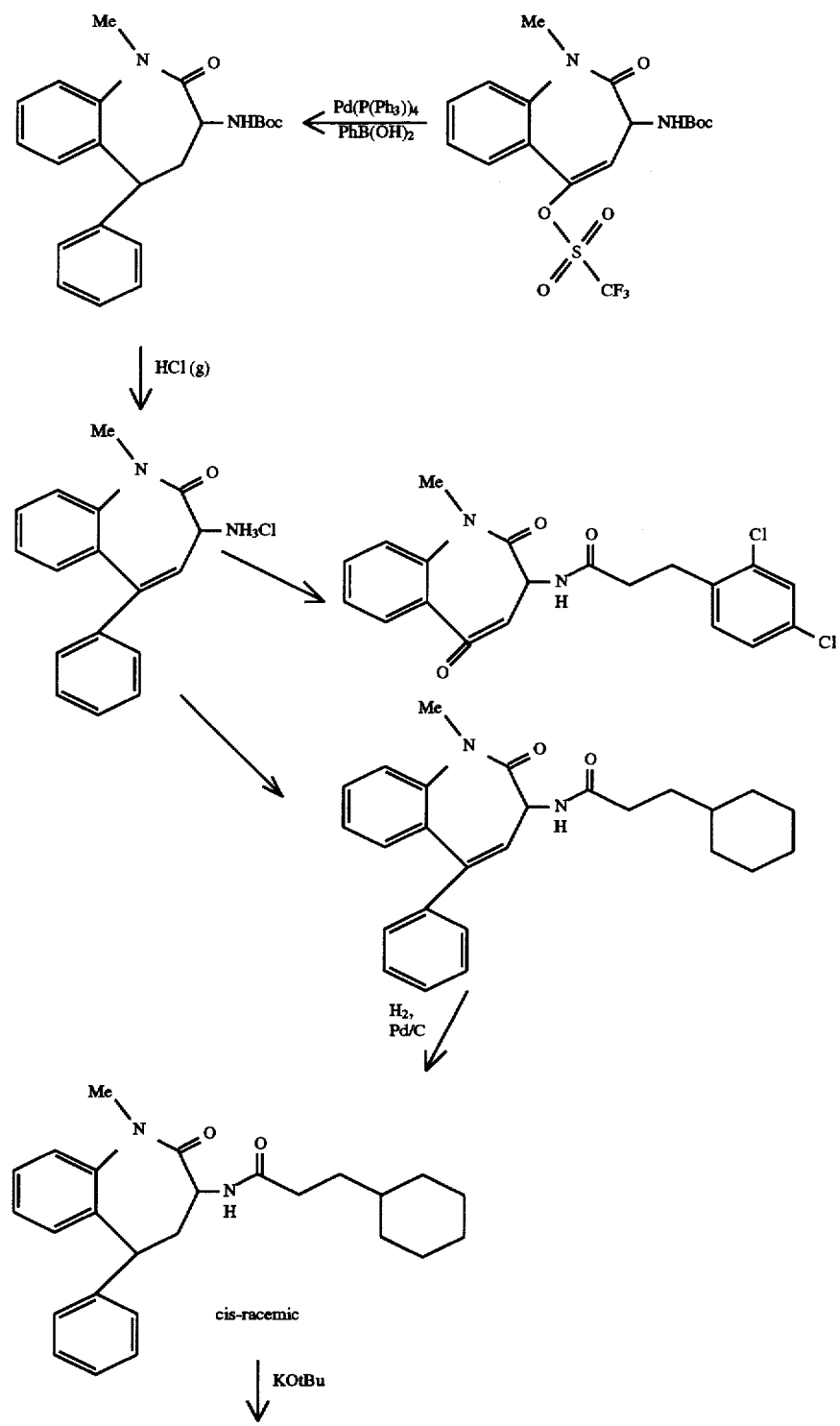

-continued
SCHEME I
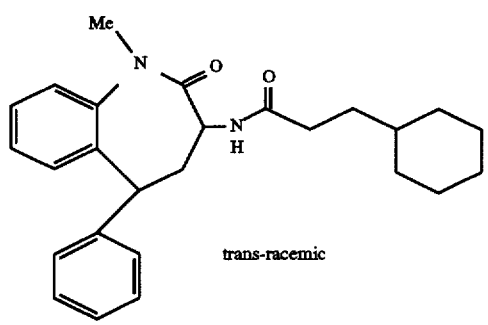
SCHEME II
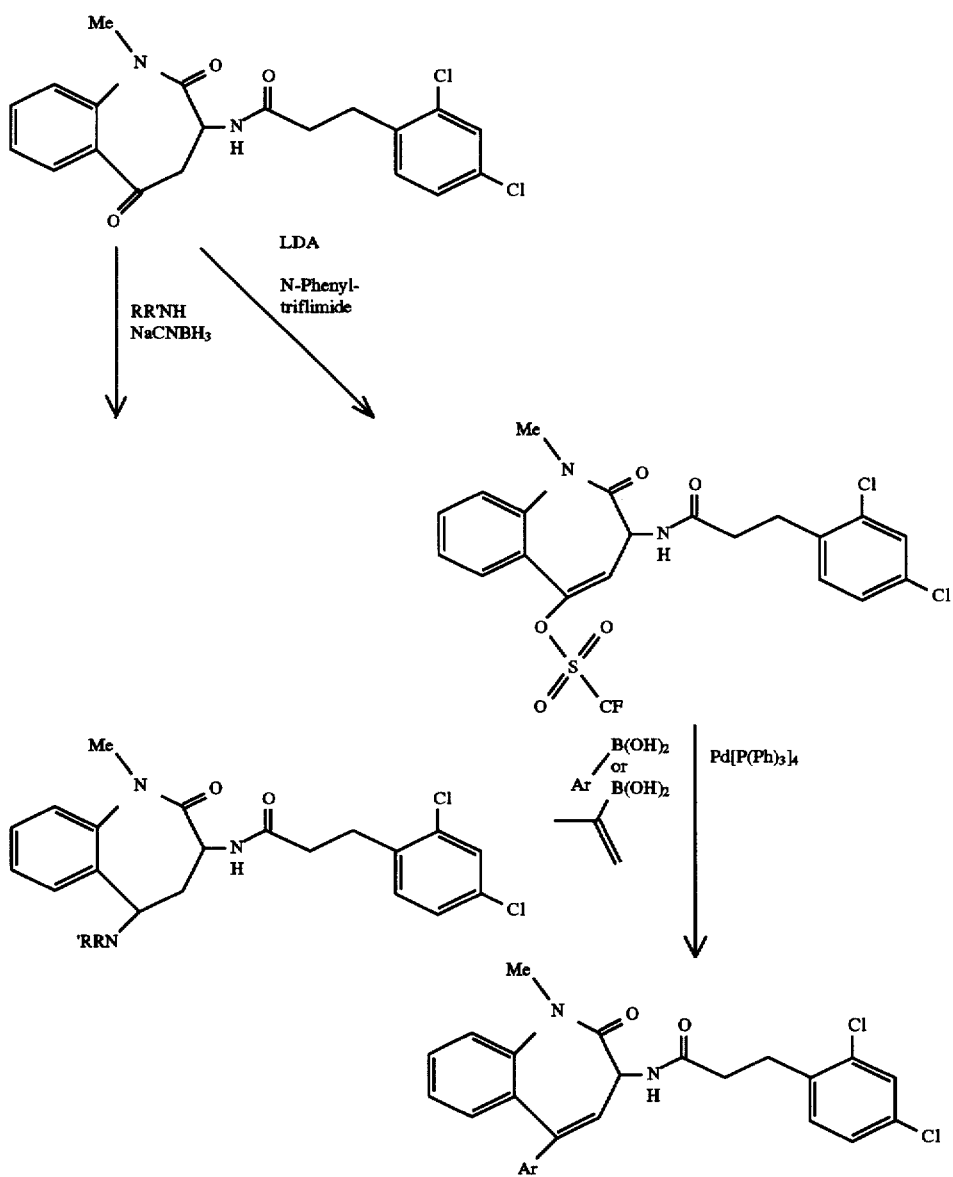

SCHEME III
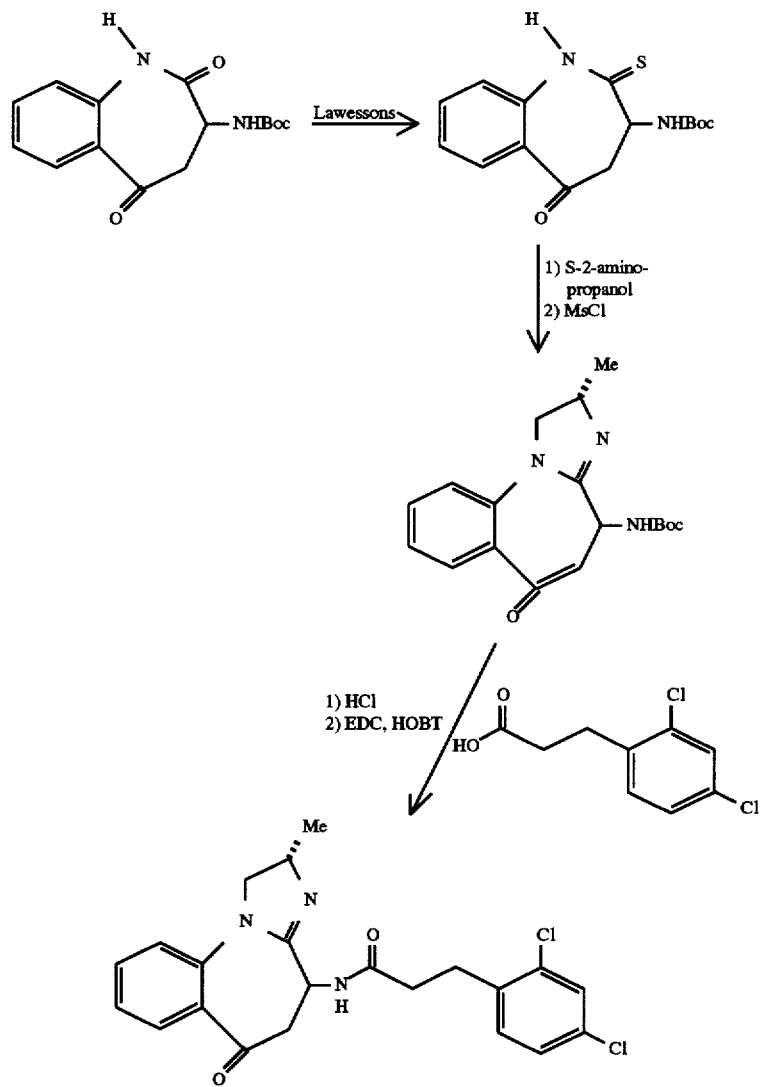
SCHEME IV
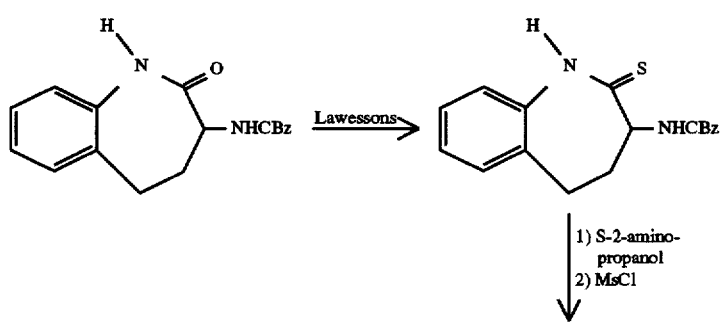

-continued
SCHEME IV

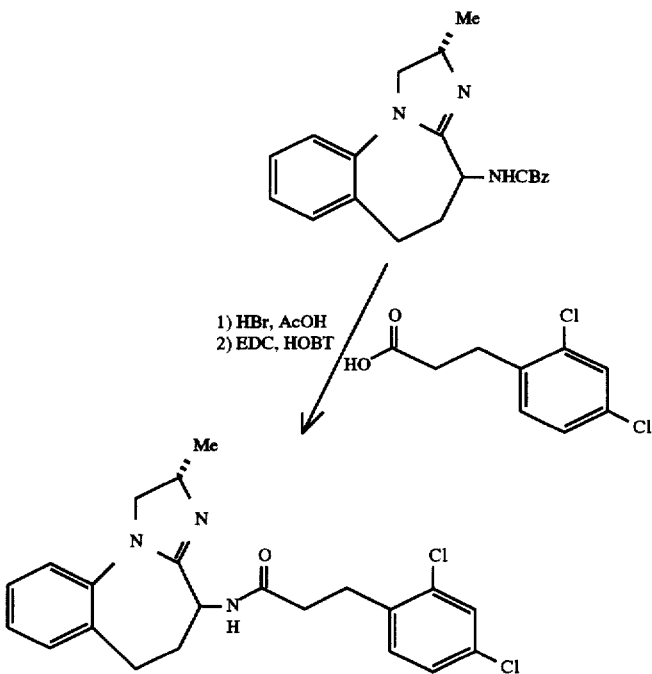

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant antiarrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salts thereof, is administered in an amount ranging from about 0.0001 to about 20 mg per kg or body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The activity of the compounds described herein as anti-arrhythmic agents is measured by their ability to block the IKs and IKr as determined by the following test protocol.

Outward potassium currents are measured in single guinea pig ventricular myocytes using a whole-cell voltage clamp technique described in detail elsewhere (Sanguinetti and Jurkiewicz, 1990, two components of cardiac delayed rectifier K+current: differential sensitivity to block by Class III antiarrhythmic agents. *J. Gen Physiol.* 96:195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl; 4KCl, 1.2 MgCl$_2$, 10 HEPES, 10 glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). I[KI] is measured as peak outward current during the voltage ramp. I[Kr] is measured as tail currents upon repolarization from −10 mV to −50 mV. I[Ks]is measured as time-dependent current during the pulse to +50 mV. Currents are measured during control, then after exposure to drug at two different concentrations.

Employing this test the compounds described herein have an IC$_{50}$ of less then 10,000 nM as IKs and/or IKr blockers.

EXAMPLE 1

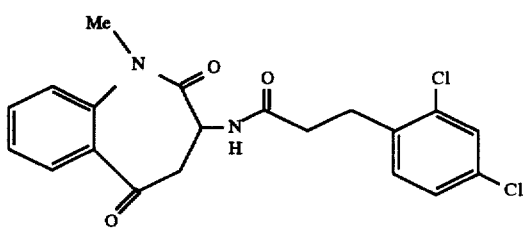

N-(1-methyl-2,5-dioxo-3,4-dihydro-1H-benzo[b]azepin-3-yl)-3-(2,4-dichlorophenyl)-propionamide
Step A:

N-(2,5-dioxo-3,4-dihydro-1H-benzo[b]azepin-3-yl)-3-(2,4 dichlorophenyl)-propionamide A 100 mL round bottom flask was charged with 3-amino-3,4-dihydro-1H-benzo[b]azepin-2,5-dione (4 g, 17.6 mmole), EDC (3.38 g, 17.6 mmole), HOBT (2.38 g, 17.6 mmole), 2,4-dichlorophenyl propionic acid (3.86 g, 17.6 mmole), Dimethylformamide (100 mL), and triethylamine (1.78 g, 17.6 mmole). The reaction mixture was stirred at room temperature for 1 hr. and then poured into saturated sodium bicarbonate (500 mL). The aqueous mixture was extracted with ethyl acetate (3×200 mL). The combined organics were dried over anhydrous magnesium sulfate, filtered, and concentrated at reduced pressure. The resulting solid was swished with a minimum of hot chloroform and filtered to give the product, 5.8 g (84%) mp 234°–236° C.
Step B:
N-(1-methyl-2,5-dioxo-3,4-dihydro-1H-benzo[b]azepin-3-yl)-3-(2,4-dichlorophenyl)-propionamide A 100 mL round bottom flask was charged with N-(2,5-dioxo-3,4-dihydro-1H-benzo[b]azepin-3-yl)-3-(2,4-dichlorophenyl)-propionamide (2.5 g, 6.38 mmole), potassium carbonate (1.76 g, 12.7 mmole), DMF (20 mL), and iodomethane (3.55 g, 25 mmole). The reaction mixture was stirred at room temperature for 5 hr. and then poured into saturated sodium bicarbonate (500 mL). The aqueous mixture was extracted with ethyl acetate (3×200 mL). The combined organics were dried over anhydrous magnesium sulfate, filtered, and concentrated at reduced pressure. The resulting solid was swished with a minimum of warm ether and filtered to give 2.1 g (81%) of the product. mp 182°–184° C.

Anal. Clacd for $C_{20}H_8N_2O_3Cl_2$: C, 59.27; H, 4.48; N, 6.91. Found: C, 59.27; H, 4.47; N, 7.11.

EXAMPLE 2

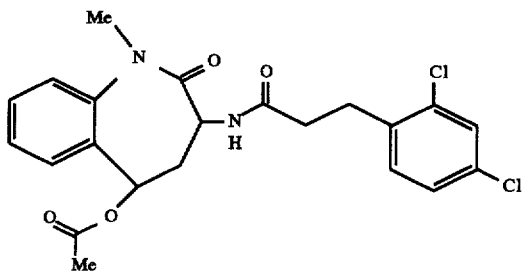

N-[1-methyl-5-acetoxy-2-oxobenzazepin-3-yl]-3-(2,4-dichlorophenyl)-propanamide

To a stirred suspension of 3-(2,4-Dichloro-phenyl)-N-(1-methyl-2,5-dioxo-2,3,4,5-tetrahydro-1H-benzo[b]azepin-3-yl)-propionamide (3.7 mmol, 1.5 g) in 15 ml EtOH and 5 ml THF was added NaBH$_4$ (3.7 mmol, 0.14 g). This was stirred at rt for 1 h. The reaction was then diluted with 200 ml EtOAc and extracted with 2×100 ml 1N HCl. The organic layer was dried with brine and evaporated under vacuum to 1.4 g of a white powder. The solid was carried on without further purification. To a stirred suspension of the above alcohol in 4 ml CH$_2$Cl$_2$ was added acetic anhydride (0.73 mmol, 75 mg, 0.07 ml), triethyl amine (0.73 mmol, 74 mg, 0.10 ml), 4-dimethylaminopyridine (0.098 mmol,11.9 mg) and the reaction was stirred at rt. The reaction mixture was then diluted with 25 ml CH$_2$Cl$_2$ and extracted with 25 ml H$_2$O, 25 ml saturated NaHCO$_3$. The organic phase was dried with brine and evaporated to a colorless oil. The resulting oil was chromatographed over silica, eluting with 20% to 50% EtOAc:Hex. The pure fractions were collected, evaporated under vacuum, taken up in CH$_2$Cl$_2$ and allowed to evaporate to dryness overnight, resulting in 110 mg of a white solid. mp 142°–144° C.

$^1$H NMR (CDCl$_3$, 300 MHz) δ7.43–7.11 (m, 7H), 6.57 (d, J=6.3 Hz, 1H), 5.94 (dd, J=11.2 and 7.8 Hz, 1H), 4.35 (m, 1H), 3.41 (s, 3H), 2.97 (t, J=7.3 Hz, 2H) 2.67 (m, 1H), 2.48 (t, J=7.3 Hz, 2H), 2.24 (m, 1H), 2.19 (s, 3H).

Anal. Calcd for $C_{22}H_{22}N_2O_4Cl_2 \cdot 0.10$ H$_2$O$\cdot$0.05 CH$_2$Cl$_2$: C, 58.16; H, 4.94; N, 6.15. Found: C, 58.18; H, 4.77; N, 6.10.

EXAMPLE 3

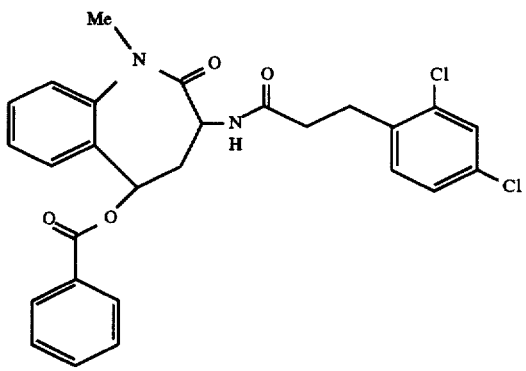

Trans-N-[1-methyl-5-benzoyloxy-2-oxobenzazepin-3-yl]-3-(2,4-dichlorophenyl)propanamide To a stirred suspension of 3-(2,4-Dichloro-phenyl)-N-(1-methyl-2,5-dioxo-2,3,4,5-tetrahydro-1H-benzo[b]azepin-3-yl)-propionamide (3.7 mmol, 1.5 g) in 15 ml EtOH and 5 ml THF was added NaBH$_4$ (3.7 mmol, 0.14 g). This was stirred at rt for 1 h. The reaction was then diluted with 200 ml EtOAc and extracted with 2×100 ml 1N HCL The organic layer was dried with brine and evaporated under vacuum to 1.4 g of a white powder. The solid was carried on without further purification. To a stirred suspension of the above alcohol in 4 ml CH$_2$Cl$_2$ was added benzoyl chloride (1.1 mmol, 0.15 g, 0.13 ml), 4-dimethylaminopyridine (0.49 mmol, 59.9 mg) and the reaction was stirred at rt. The reaction mixture was then diluted with 25 ml CH$_2$Cl$_2$ and extracted with 25 ml H$_2$O. The organic phase was dried with brine and evaporated to a colorless oil. The resulting oil was chromatographed over silica, eluting with 20%0 EtOAc:Hex. The pure fractions were collected, evaporated under vacuum, crystallized from EtOAc:Hex to give 169 mg of a white solid. mp 171°–173° C. $^1$H NMR (CDCl$_3$, 300 MHz) δ8.15 (d, J=7.1 Hz, 2H), 7.67–7.10 (m, 10H), 6.62 (d, J=6.6 Hz, 1H), 6.21 (dd, J=7.8 and 11.2), 4.48–4.39 (m, 1H), 3.46 (s, 3H), 2.98 (t, J=7.3 Hz, 2H), 2.89 (m, 1H), 2.50 (t, J=7.3 Hz, 2H), 2.41–2.31 (m, 1H).

Anal. Calcd for $C_{27}H_{24}N_2O_4Cl_2 \cdot 0.30H_2O$: C, 62.75; H, 4.80; N, 5.42. Found: C, 62.78; H, 4.79; N, 5.32.

EXAMPLE 4

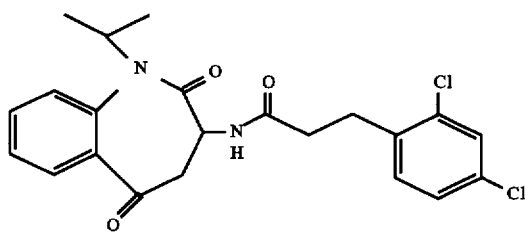

N-isopropyl-2,5-dioxo-3,4-dihydro-1H-benzo[b]azepin-3-yl)-3-(2,4-dichlorophenyl)-propionamide A 100 mL round bottom flask was charged with N-(2,5-dioxo-3,4-dihydro-1H-benzo [b]azepin-3-yl)-3-(2,4-dichlorophenyl)-propionamide (1.95 g, 5 mmole), potassium carbonate (1.38 g, 10 mmole), DMF (20 mL), and 2-iodopropane (3.5 g, 20 mmole). The reaction mixture was stirred at room temperature for 24 hr. and then poured into saturated sodium bicarbonate (200 mL). The aqueous mixture was extracted with ethyl acetate (3×100 mL). The combined organics were dried over anhydrous magnesium sulfate, filtered, and concentrated at reduced pressure. The residue was chromatographed on silica gel eluting with 40% ethylacetate/hexane to give 1.4 g of product. (64%) mp 107°–109° C.

Anal. Clacd for $C_{22}H_{22}N_2O_3Cl_2$: C, 60.98; H, 5.12; N, 6.46. Found: C, 61.18; H, 5.13; N, 7.11.

EXAMPLE 5

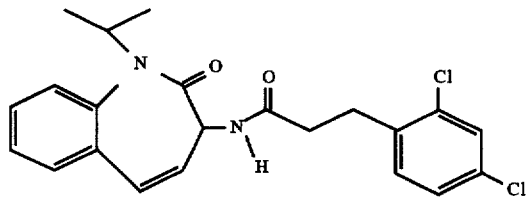

N-(1-(2-propyl)-2-oxobeozazepin-3-yl)-3-(2,4-dichlorophenyl) propanamide

To a stirred solution of N-(1-(2-propyl)-2,5-idioxo-benzazepin-3-yl)-3-(2,4-dichlorophenyl) propanamide (0.50 g, 1.15 mmol) in ethanol (25 ml) was added sodium borohydride (87 mg, 2.31 mmol). After 15 minutes, the mixture was diluted with ethyl acetate (100 ml) and saturated aqueous sodium hydrogen carbonate (200 ml). The organic layer was separated and the aqueous layer was extracted again with ethyl acetate (2×100 ml). The organic layers were combined and condensed in vacuo. The resulting oil was crystallized from ethyl acetate/hexane, yielding a white solid (435 mg, 87%). This solid was then dissolved in methylene chloride (30 ml). To this was added triethylamine (167 µl, 1.20 mmol) and then methanesulfonylchlofide (93 µl, 1.20 mmol). After one hour, the mixture was diluted with ethyl acetate (100 ml) and saturated aqueous sodium hydrogen carbonate (200 ml). The organic layer was separated and the aqueous layer was extracted again with ethyl acetate (2×100 ml). The organic layers were combined and condensed in vacuo. A portion of the resulting foam (100 mg, 0.20 mmol) was then dissolved in toluene (5 ml) and to this was added catalytic p-toluenesulfonic acid (30 mg), and the mixture was heated to 100° C. for one and one half hours. The mixture was then cooled to room temperature, diluted with ethyl acetate (75 ml) and saturated aqueous sodium hydrogen carbonate (100 ml). The organic layer was separated and the aqueous layer was extracted again with ethyl acetate (2×50 ml). The organic layers were combined and condensed in vacuo. The resulting oil was chromatographed over silica with 1:3 ethyl acetate/hexane, yielding a white solid (35 mg, 43%). m.p. 142°–143° C. $^1$H NMR δ7.38–7.05 (m, 8H), 6.68 (dd, J=2.2, 9.8 Hz, 1H), 5.70 (dd, J=6.4, 9.8 Hz, 1H), 4.50–4.40 (m, 2H), 3.06 (t, J=7.4 Hz, 2H), 2.60 (t, J=7.8 Hz, 2H), 2.60 (t, J=7.4 Hz, 2H), 1.45 (d, J=6.8 Hz, 3H), 1.16 (d, J=6.8 Hz, 3H). Anal. Calcd. for $C_{22}H_{22}N_2O_2Cl_2$: C, 63.32; H, 5.31; N, 6.71. Found: C, 63.16; H, 5.24; N, 6.84%.

EXAMPLE 6

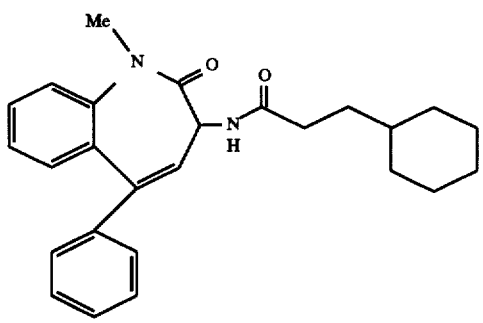

N-(2,3-Dihydro-2-oxo-1-methyl-5-phenyl-1H-benzazepin-3-yl)-3-cyclohexyl-propanamide Step A:
Preparation of 1-methyl-3-tertbutyloxycarbonylamino-2,3,4,5-tetrahydro-2,5-dioxobenzazepine A solution of 3-tertbutyloxycarbonylamino-2,3,4,5-tetrahydro-2,5-dioxobenzo[b]azepine (5 g, 17.2 mmole) in DMF (50 mL) was treated with potassium carbonate (4.76 g, 34.4 mmole) and methyl iodide (4.88 g, 34.4 mmole). The reaction was stirred at ambient temperature for 4 hours. The mixture was diluted with ethyl acetate (300 ml) and saturated aqueous sodium hydrogen carbonate (500 ml). The organic layer was separated and the aqueous layer was extracted again with ethyl acetate (2×300 ml). The organic layers were combined, dried over anhydrous magnesium sulfate, filtered and concentrated in vacuo. The resulting solid was swished with warm ethyl ether (200 mL) and collected by filtration to give 4.1 g of the product. mp 205°–206° C.

$^1$H NMR (300 MHz, CDCl$_3$) δ7.60–7.50 (m, 2H), 7.35–7.20 (m, 2H), 5.77 (m, 1H), 4.9 (m, 1H), 3.41 (s, 3H), 3.33 (rid, J=3.5, 12.5 Hz), 3.33 (dd, J=12.5, 18 Hz), 1.43 (s, 9H).

Step B:
Preparation of 5-phenyl 3-(tert-butoxycarbonylamino)-1-methyl-2-oxo-2,3-dihydro-1H -benzo[b]azepine A solution of 1-methyl-3-tertbutyloxycarbonylamino-2,3,4,5-tetrahydro-2,5-dioxobenzazepine (3 g, 9.8 mmole) in THF (100 mL) at 0° C. was treated with a solution of LDA in THF (7 mL of 2N soln). The reaction was stirred at 0° C. for five minutes and a solution of N-phenyltriflimide (3.92 g, 11 mmole) in THF (10 mL) was added. The reaction was stirred at 0° C. for 1.5 hr and then poured into saturated sodium bicarbonate (800 mL). The aqueous mixture was extracted with ethyl acetate (3×200 mL). The combined organics were dried over anhydrous magnesium sulfate, filtered, and concentrated at reduced pressure. The residue was chromatographed on silica gel eluting with 25% ether/hexanes then rechromatographed using 2%–10% ethylacetate/chloroform as eluent to give 2.4 g of product. (64%).

The material thus obtained was dissolved in dimethoxyethane (70 mL), and treated with 7.5 mL of a 2N solution of sodiumcarbonate, phenyl boronic acid (932 mg, 7.6 mmole), palladium tetrakistriphenylphophine (329 mg, 0.28 mmole), and LiCl (966 mg, 22.7 mmole). The reaction mixture was then heated to reflux for 2.5 hr. the reaction was cooled to room temperature and then poured into saturated sodium bicarbonate (800 mL). The aqueous mixture was extracted with ethyl acetate (3×200 mL). The combined organics were dried over anhydrous magnesium sulfate, filtered, and concentrated at reduced pressure. The residue was chromatographed on silica gel eluting with 30% ethyl acetate/hexanes to give 1.68 g of the product. (63%). $^1$H NMR (300 MHz CDCl$_3$) δ7.5–7.10 (m, 9H), 6.11 (d, J=3.1 Hz, 1H), 5.9 (d, J=5.6 Hz, 1H), 4.45 (m, 1H), 3.46 (s, 3H), 1.44 (s, 9H).

Step C:
Preparation of 5-phenyl-3-amino)-1-methyl-2-oxo-2,3-dihydro-1H-benzo[b]azepine hydrochloride A solution of 5-phenyl 3-(tert-butoxycarbonylamino)-1-methyl-2-oxo-2,3-dihydro-1H-benzo[b]azepine prepared as described above 1.8 g (4.9 mmole) in ethyl acetate was treated with excess gaseous HCl until all the starting material was consumed. The reaction was then concentrated at reduced pressure and the solid collected to give the product 1.4 g (95%) mp 194°–200° C.

Step D:
Preparation of N-(2,3-Dihydro-2-oxo-1-methyl-5-phenyl-1H-1benzazepin-3-yl)-3-cyclohexyl-propanamide To a stirred solution of 3-amino-5-phenyl-1-methyl-2-oxo-2,3-dihydro-1H-benzo[b]azepin hydrochloride salt (0.50 g, 1.66 mmol) in N,N-dimethylformamide (25 ml) was added 3-cyclohexylpropionic acid (311 mg, 2.0 mmol), 1-(3-dimethylaminopropyl)-3-ethylcarbodiimide hydrochloride (381 mg, 2.0 mmol), 1-hydroxybenzotriazole hydrate (269 mg, 2.0 mmol), and triethylamine (277 ml, 2.0 mmol). After three hours, the mixture was diluted the ethyl acetate (100 ml) and saturated aqueous sodium hydrogen carbonate (200 ml). The organic layer was separated and the aqueous layer was extracted again with ethyl acetate (2×100 ml). The organic layers were combined and condensed in vacuo. The resulting oil was chromatographed over silica with 3:7 ethyl acetate/hexane. Upon removal of eluent in vacuo, a white solid was recovered (0.540 mg, 81%). m.p. 219°–220° C. $^1$H NMR δ7.45–7.12 (m, 9H), 7.07 (d, J=6.1 Hz, 1H), 5.91 (d J=5.4 Hz, 1H), 4.62 (t, J=5.8 Hz, 1H), 3.48 (s, 3H), 2.33 (t, J=6.3 Hz, 2H), 1.80–1.52 (m, 7H), 1.38–1.10 (m, 4H), 1.00–0.82 (m, 2H).

Anal. Calcd. for C$_{26}$H30N$_2$O$_2$.0.75 H$_2$O: C, 76.38; H, 7.57, N, 6.85. Found: C, 76.29; H, 7.36, N, 6.95%.

EXAMPLE 7

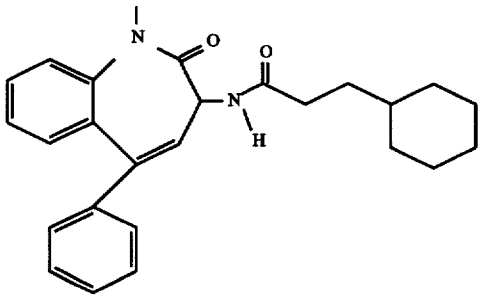

cis-N-(2,3,4,5-tetrahydro-2-oxo-1-methyl-5-phenyl-1H-benzazepin-3-yl)-3-cyclohexylpropanamide A solution of N-(2,3-Dihydro-2-oxo-1-methyl-5-phenyl-1H-1-benzazepin-3-yl)-3-cyclohexyl-propanamide (250 mg) in methanol (20 ml) was added to a suspension of 10% palladium on carbon (100 mg) in methanol (20 ml). This mixture was subjected to 50 psi of hydrogen on a Parr shaker for two hours. The mixture was then filtered over celite and concentrated at reduced pressure. The resulting foam was crystallized from a mixture of ethyl acetate and hexane, yielding a white solid (200 mg, 80%), which is a cis, racemic mixture. m.p. 156°–158° C.

$^1$H NMR δ7.45–7.02 (m, 9H), 6.72 (s, 1H), 4.61–4.49 (m, 1H), 4.20 (d, J=7.5 Hz, 1H), 3.23–3.10 (m, 1H), 2.62–2.51 (m, 1H), 2.21 (t, J=8.3 Hz, 2H), 1.75–1.44 (m, 8H), 1.30–1.05 (m, 3H), 0.96–0.78 (m, 2H).

Anal. Calcd. for C$_{26}$H$_{32}$N$_2$O$_2$: C, 77.19; H, 7.97; N, 6.92. Found: C, 77.19; H, 7.93; N, 7.02%.

EXAMPLE 8

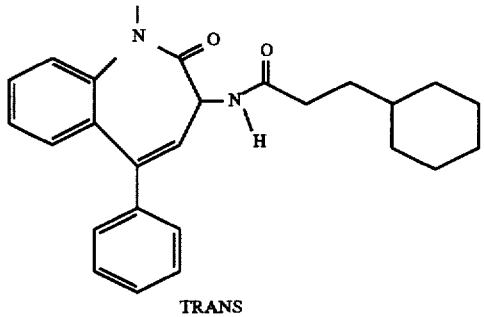

TRANS trans-N-(2,3,4,5-tetrahydro-2-oxo-1-methyl-5-phenyl-1H-benzazepin-3-yl)-3-cyclohexylpropanamide Epimerization of the cis isomer to the trans isomer was accomplished by adding potassium t-butoxide (75 mg, 0.67 mmol) to a solution of cis-N-(2,3,4,5-tetrahydro-2-oxo-1-methyl-5-phenyl-1H-benzazepin-3-yl)-3-cyclohexylpropanamide (90 mg, 0.22 mmol) in tetrahydrofuran (10 ml) and heating to 50° C. for 18 hours. The mixture was diluted with ethyl acetate (50 ml) and saturated aqueous sodium hydrogen carbonate (100 ml). The organic layer was separated and the aqueous layer was extracted again with ethyl acetate (2×40 ml). The organic layers were combined and concentrated at reduced pressure. The resulting mixture of isomers was crystallized from a mixture of ethyl acetate and hexane, from which was obtained the desired trans isomer (35 mg, 39%). m.p. 185°–186° C. $^1$H NMR δ 7.40–7.09 (m, 8H), 6.74 (d, J=8.4 Hz, 1H), 6.61 (d, J=6.6 Hz, 1H), 4.60–4.50 (m, 1H), 4.32–4.22 (m, 1H), 3.51 (s, 3H), 3.33–3.10 (m, 1H), 2.21 (t, J=7.8 Hz, 2H), 2.15–2.02 (m, 1H), 1.76–1.44 (m, 5H), 1.30–1.15 (m, 4H), 0.96–0.80 (m, 2H). Anal. Calcd. for C$_{26}$H32N$_2$O$_2$.H$_2$O: C, 76.01; H, 8.02; N, 6.82. Found: C, 76.00; H, 7.75; N, 6.91%.

EXAMPLE 9

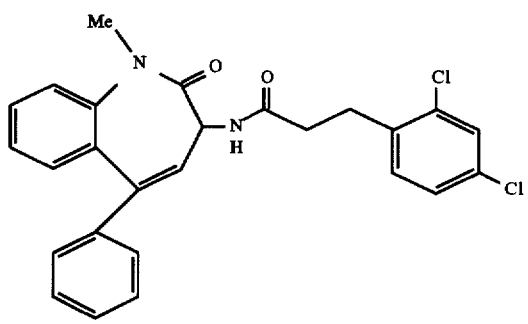

1-(N-(2,3-Dihydro-2-oxo-1-methyl-5-phenyl-1H-1 benzazepin-3-yl)-(2,4-dichlorophenyl-propanamide To a stirring solution of 3-amino-5-phenyl-1-methyl-2-oxo-2,3-dihydro-1H-benzo[b]azepin hydrochloride salt (0.66 mmol, 0.2 g) in 5 ml DMF was added EDC: (1.3 mmol, 0.25 g), HOBT (1.3 mmol, 0.18 g), 2,5-dichlorophenyl-propionic acid (1.3 mmol,0.29 g), triethylamine (1.3 mmol, 0.13 g) and the reaction was stirred at rt for 1 h. The reaction was then diluted with 100 ml saturated NaHCO$_3$ and extracted with 2×50 ml EtOAc. The combined organic layers were dried with Na$_2$SO$_4$ and evaporated under vacuum. The residue was chromatographed over silica, eluting with 20% to 50% EtOAc:Hex. The pure fractions were collected, evaporated under vacuum and crystallized from Et$_2$O to give 0.22 g of a fluffy white solid. mp 102°–104° C.: $^1$H NMR (300 MHz, CDCl$_3$) δ7.44–7.14 (m, 12H), 7.05 (d, J=6.4 Hz, 1H), 5.79 (d, J=5.1 Hz, 1H),4.58 (t, J=5.6 Hz, 1H), 3.47 (s, 3H),3.09 (t, J=7.6 Hz, H), 2.63 (t, J=7.6 Hz, 2H). Anal. Calcd for C$_{26}$H$_{22}$N$_2$O$_2$Cl$_2$.0.50 H$_2$O: C, 65.93; H, 4.89; N, 5.91. Found: C, 65.85; H, 4.77; N, 5.78.

EXAMPLE 10

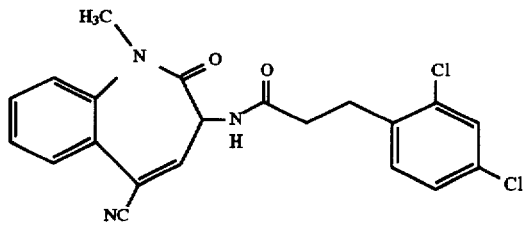

N-(5-Cyano-1-methyl-2-oxo-2,3-dihydro-1H-benzo[b]azepin-3-yl)-3-(2,4- dichloro-phenyl)-propionamide
Step A:
3-[3-(tert-butoxycarbonylamino)-5-cyano-1-methyl-2-oxo-2,3-dihydro-1H-benzo[b]azepin To a stirred solution of the trifluoromethane sulfonic acid 3- [3-(tert-butoxycarbonylamino-1-methyl-2-oxo-2,3-dihydro-1H-benzo[b]azepin-5-yl ester (0.2 g, 0.46 mmol) in anhydrous DMF was added the Pd[PPh$_3$]$_4$ (0,069 mmol, 79.7 mg) and Zn(CN)$_2$ (0.92 mmol, 0.11 g). The reaction was heated to 80° C. for 0.5h, cooled to rt. and diluted with 100 ml H$_2$O. This was extracted with 2×50 ml EtOAc. The combined organic layers were dried with brine and Na$_2$SO$_4$. The extracts were evaporated under vacuum to an orange oil which became a solid on standing. This was chromatographed over silica eluting with 50% EtOAc:Hex, giving 109 mg of a pale yellow solid, 80%. $^1$H NMR (300 MHz, CDCl$_3$) δ7.75–7.26 (m,4H), 6.67 (d, J=5.1 Hz, 1H), 6.12 (d, J=6.4 Hz, 1H), 4.45 (t, J=5.8 Hz, 1H), 3.44 (s,3H), 1.44 (s, 9H).

Step B:
Preparation of N-(5-Cyano-1-methyl-2-oxo-2,3-dihydro-1H-benzo[b]azepin-3-yl)-3-(2,4-dichloro-phenyl)-propionamide To a stirring solution of the 3-[3-(tert-butoxycarbonylamino)]-5-cyano-1-methyl-2-oxo-2,3-dihydro-1H-benzo [b]azepin (0.35 mmol, 0.11 g) in 5 ml EtOAc was bubbled HCl gas for 0.5 h, resulting in precipitate formation. The reaction mixture was evaporated under vacuum to 85.7 mg of a yellow solid which was carried on without further purification.

To a stirring solution of 3-amino-5-cyano-1-methyl-2-oxo-2,3-dihydro-1H-benzo[b]azepin hydrochloride salt (0.34 mmol, 85 mg) under an argon atmosphere in 2 ml DMF was added the 2,4-(dichlorophenyl)-propionic acid (0.51 mmol, 0.11 g), EDC (0.51 mmol, 97.9 mg), HOBT (0.51 mmol, 68.9 mg), and triethyl amine (0.34 mmol, 0.05 ml). This was stirred at rt for 1 h. The reaction was diluted with 50 ml saturated sodium bicarbonate and extracted with 2×20 ml EtOAc. The combined organics were washed with 10% KHSO$_4$, dried with brine and Na$_2$SO$_4$, and evaporated under vacuum. The resulting lavender solid was chromatographed over silica, eluting with 20% to 70% EtOAc:Hex to give 72 mg of a white solid. mp=151°–154° C. $^1$H NMR (300 MHz, CDCl$_3$) δ7.71 (d, J=7.8 Hz, 1H), 7.56–7.15 (m, 7H), 7.02 (d, J=4.7 Hz, 1H), 6.49 (d, J=5.4 Hz, 1H), 4.57 (t, J=5.4 Hz, 1H), 3.45 (s, 3H), 3.05 (d, J=7.6 Hz, 2H), 2.62 (d, J=7.8 Hz, 2H). Anal. Calcd. for C$_{21}$H$_{17}$Cl$_2$N$_3$O$_2$.0.05 hex. 1.10 H$_2$O C, 60.86; H, 4.29; N, 10.00. Found: C, 60.89; H, 4.20; N, 9.96.

EXAMPLE 11

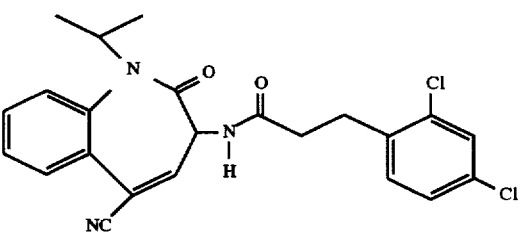

N-(5-Cyano-1-(2-propyl)-2-oxo-2,3-dihydro-1H-benzo[b]azepin-3-yl)-3-(2,4-dichloro-phenyl)-propionamide To a stirring solution of 3-(2,4 Dichloro-phenyl)-N-(1-(2-propyl)-2,5-dioxo-2,3,4,5-tetrahydro-1H-benzo [b]azepin-3-yl)-propionamide (0.81 mmol, 0.35 g) in THF (5 ml) cooled in an ice bath was added LDA (1.1 mmol, 0.56 ml of a 2M solution) dropwise and stirred for 5 mins. To this solution was added N-phenyltrifluoromethylsulfonimide (1.1 mmol, 0.39 g) and the reaction stirred in ice for 1 h. The reaction was diluted with 50 ml H$_2$O and extracted with 2×25 ml EtOAc. The combined organics were dried with brine and Na$_2$SO$_4$. This was evaporated to a yellow oil which was carried on without further purification.

The above oil was taken up in 5 ml DMF. To this solution was added Pd[PPh$_3$]$_4$ (0.26 mmol, 0.31 g), Zn(CN)$_2$ (1.1 mmol, 0.12 g) and the reaction was heated to 80° C. for 0.5 h. The reaction was cooled to rt, diluted with saturated Na$_2$CO$_3$, and extracted with 2×50 ml EtOAc. The combined 5 organics were dried with brine, Na$_2$SO$_4$ and evaporated under vacuum. The residue was chromatographed over silica, eluting with 20% to 70% EtOAc:Hex. The pure fractions were collected, evaporated under vacuum, and crystallized from ethyl ether to give 100 mg of a pale yellow solid. mp 103°–106° C. $^1$H NMR (300 MHz, CDCl$_3$) δ7.72–7.02 (m, 8H), 6.50 (d, J=5.3 Hz, 1H), 4.53 (h, J=6.8 Hz, 1H), 3.04 (t, J=7.3 Hz, 2H), 2.61 (t, J=7.3 Hz, 2H), 1.47 (d, J=6.8 Hz, 3H), 1.19 (d, J=6.8 Hz, 3H). Anal. Calcd for C$_{23}$H$_{21}$N$_3$O$_2$Cl$_2$.0.05 Et$_2$O. 0.30 H$_2$O: C, 61.72; H, 4.93; N, 9.31. Found: C, 61.74; H, 4.74; N, 9.22.

EXAMPLE 12

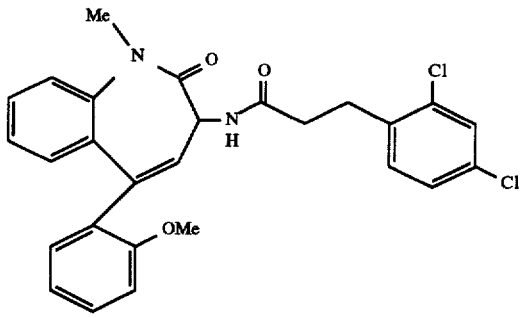

3-(2,4-Dichloro-phenyl)-N-[5-(2-methoxy-phenyl)-1-methyl-2-oxo-2,3-dihydro-1H-benzo[b]azepin-3-yl-propanamide Step A To a stirring solution of 3-(2,4-Dichloro-phenyl)-N-(1-methyl-2,5-diox-2,3,4,5-tetrahydro-1H-benzo[b]azepin-3-yl)-propionamide (7.1 mmol, 2.88 g) in 58 ml THF cooled in an ice bath was added the LDA (9.9 mmol, 5.M of a 2M heptane/THF/ethylbenzene soln) dropwise and the solution stirred for 5 min. To this was added N-phenyltrifluoromethylsulfonimide (9.9 mmol, 3.54 g) and the reaction stirred in an ice bath for 1 h. The reaction was diluted with 200 ml H$_2$O and extracted with 2×100 ml EtOAc. The combined organics were dried with brine and Na$_2$SO$_4$ and evaporated under vacuum to a pale yellow solid. $^1$H NMR (300 MHz, CDCl$_3$) δ7.72–6.99 (m, 8H), 5.80 (d, J=4.9 Hz, 1H), 4.44 (t, J=5.6 Hz, 1H), 3.44 (s, 3H), 3.05 (t, J=7.6 Hz, 2H), 2.61 (t, J=7.6 Hz, 2H).

Step B

To a stirring solution of trifluoromethane sulfonic acid 3-[3-(2,4-dichlorophenyl)-propionylamino]-1-methyl-2-oxo-2,3-dihydro-1H-benzo[b]azepin-5-yl ester (0.37 mmol, 0.2 g) in 7 ml DME was added the Na$_2$CO$_3$ (0.74 mmol, 0.37 ml of a 2M aqueous solution), Pd[PPh$_3$]$_4$ (0.037 mmol, 42.7 mg), LiCl (1.1 mmol,47.1 mg), o-methoxyphenylboronic acid (0.74 mmol, 0.11 g), and the reaction heated to reflux for 2 h. After 2 h o-methoxyphenylboronic acid (0.74 mmol, 0.11 g), and Pd[PPh$_3$]$_4$ (0.019 mmol, 21.4 mg) were added and heating continued for 2 h. The reaction was cooled to rt, diluted with 30 ml saturated NaHCO$_3$ and extracted with 2×20 ml EtOAc. The combined organics were washed with 10% KHSO$_4$, dried with brine, Na$_2$SO$_4$ and evaporated under vacuum. This residue was chromatographed over silica elutiong with 20% to 40% EtOAc:Hex. The pure fractions were collected and evaporated to a colorless oil which crystallized from Et$_2$O to give 65 mg of a white solid. mp 203°–205° C.: $^1$H NMR (300 MHz, CDCl$_3$) δ7.37–6.98 (m, 8H), 6.84 (d, J=7.6 Hz, 1H), 5.68 (d, J=5.1 Hz, 1H), 4.63 (t, J=5.3 Hz, 1H), 3.50 (s, 3H), 3.48 (s, 3H), 3.08 (t, J=7.3 Hz, 2H), 2.62 (t, J=7.3 Hz, 2H) Anal. Calcd for C$_{27}$H$_{24}$Cl$_2$N$_2$O$_3$.0.25 H$_2$O: C, 64.87; H, 4.94; N, 5.60. Found: C, 64.81; H, 4.78; N, 5.83.

EXAMPLE 13

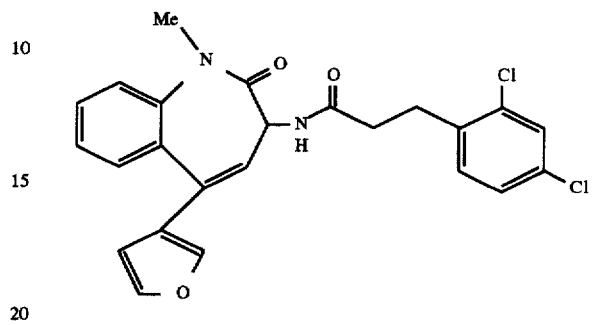

3-(2,4-Dichloro-phenyl)-N-[5-(3-furyl)-1-methyl-2-oxo-2,3-dihydro-1H-benzo[b]azepin-3-yl]-propanamide Step A To a stirring solution of 3-(2,4-Dichloro-phenyl)-N-(1-methyl-2,5-dioxo-2,3,4,5-tetrahydro-1H-benzo[b]azepin-3-yl)-propionamide (7.1 mmol, 2.88 g) in 58 ml THF cooled in an ice bath was added the LDA (9.9 mmol, 5.0 ml of a 2M heptane/THF/-ethylbenzene soln) dropwise and the solution stirred for 5 min. To this was added N-phenyltrifluoromethyl-sulfonimide (9.9 mmol, 3.54 g) and the reaction stirred in an ice bath for 1 h. The reaction was diluted with 200 ml H$_2$O and extracted with 2×100 ml EtOAc. The combined organics were dried with brine and Na$_2$SO$_4$ and evaporated under vacuum to a pale yellow solid. $^1$H NMR (300 MHz, CDCl$_3$) δ7.72–6.99 (m, 8H), 5.80 (d, J=4.9 Hz, 1H), 4.44 (t, J=5.6 Hz, 1H), 3.44 (s, 3H), 3.05 (t, J=7.6 Hz, 2H), 2.61 (t, J=7.6 Hz, 2H).

Step B

To a stirring solution of trifluoromethane sulfonic acid 3-[3-(2,4-chlorophenyl)-propionylamino]-1-methyl-2-oxo-2,3-dihydro-1H-benzo[b]azepin-5-yl ester (0.37 mmol, 0.2 g) in 7 ml DME was added the Na$_2$CO$_3$ (0.74 mmol, 0.37 ml of a 2M aqueous solution), Pd[PPh$_3$]$_4$ (0.037 mmol, 42.7 mg), LiCl (1.11 mmol, 47.1 mg), (3-furyl)-boronic acid and the mixture heated to reflux for 2 h. The reaction was cooled to rt, diluted with 50 ml saturated NaHCO$_3$, and extracted with 2×30 ml EtOAc. The combined organics were washed with KHSO$_4$, dried with brine, Na$_2$SO$_4$ and evaporated under vacuum. The residue was chromatographed over silica, eluting with 30% to 40% EtOAc:Hex. The pure fractions were collected, evaporated under vacuum, and crystallized from Et$_2$O to give 3C) 85.0 mg of a white solid. mp 114°–117° C. $^1$H NMR (300 MHz, CDCl$_3$) δ7.59–7.15 (m, 8H), 7.02 (d, J=4.2 Hz, 1H), 6.46–6.45 (m, 1H), 5.77 (d, J=5.6 Hz, 1H), 4.57 (t, J=5.9 Hz, 1H), 3.44 (s, 3H), 3.07 (t, J=7.6 Hz, 2H), 2.62 (t, J=7.6 Hz, 2H). Anal. Calcd for C$_{24}$H$_{21}$N$_2$O$_3$Cl$_2$.0.20 H$_2$O: C, 62.67; H, 4.69; N, 6.09. Found: C, 62.62; H, 4.49; N, 5.84.

EXAMPLE 14

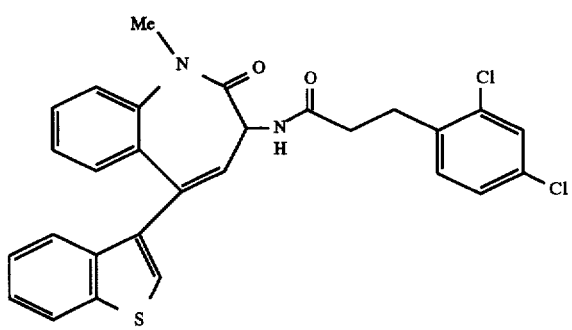

3-(2,4-Dichloro-phenyl)-N-[5-benzothiophene-3-yl)-1-methyl-2-oxo 2,3-dihydro-1H-benzo [b]azepin-3-yl]-propanamide

Step A

To a stirring solution of 3-(2,4-Dichloro-phenyl)-N-(1-methyl-2,5-dioxo-2,3,4,5-tetrahydro-1H-benzo[b]azepin-3-yl)-propionamide (7.1 mmol, 2.88 g) in 58 ml THF cooled in an ice bath was added the LDA (9.9 mmol, 5.0 ml) of a 2M heptane/THF/ethylbenzene soln) dropwise and the solution stirred for 5 min. To this was added N-phenyltrifluoromethylsulfonimide (9.9 mmol, 3.54 g) and the reaction stirred in an ice bath for 1 h. The reaction was diluted with 200 ml H$_2$O and extracted with 2×100 ml EtOAc. The combined organics were dried with brine and Na$_2$SO$_4$ and evaporated under vacuum to a pale yellow solid. $^1$H NMR (300 MHz, CDCl$_3$) δ7.72–6.99 (m, 8H), 5.80 (d, J=4.9 Hz, 1H), 4.44 (t, J=5.6 Hz, 1H), 3.44 (s, 3H), 3.05 (t, J=7.6 Hz, 2H), 2.61 (t, J=7.6 Hz, 2H).

Step B

To a stirring solution of trifluoromethane sulfonic acid 3-[3-(2,4-dichlonohenyl)-propionylaminol-1-methyl-2-oxo-2,3-dihydro-1H-benzo[b]azepin-5-yl ester (0.37 mmol, 0.2 g) in 7 ml DME was added the Na$_2$CO$_3$ (0.74 mmol, 0.37 ml of a 2M aqueous solution), Pd[PPh$_3$]$_4$ (0.037 mmol, 42.7 mg), LiC$_1$ (1.11 mmol,47.1 mg), (3-benzothiophene) boronic acid (1.48 mmol, 0.26 g) and the mixture heated to reflux for 2 h. The reaction was cooled to rt, diluted with 100 ml H$_2$O and extracted with 2×50 ml EtOAc. The combined organics were dried with Na$_2$SO$_4$ and evaporated under vacuum. This residue was chromatographed over silica, eluting with 25% EtOAc:Hex. The pure fractions were collected, evaporated under vacuum and crystallized from Et$_2$O to give 90 mg of a beige solid. mp 179.5°–181° C.: $^1$H NMR (300 MHz, CDCl$_3$) δ7.90–7.86 (m, 1H), 7.44–7.07(m, 11H), 5.91 (d, J=5.1 Hz, 1H), 4.67 (t, J=5.4, 1H), 3.56 (s, 3H), 3.10 (t, J=7.3 Hz, 2H), 2.65 (t, J=7.3 Hz, 2H). Anal. Calcd for C$_{28}$H$_{22}$Cl$_2$N$_2$O$_2$S.0.30 H$_2$O: C, 63.83; H, 4.32; N, 5.32. Found: C, 63.80; H, 4.25; N, 5.12.

EXAMPLE 15

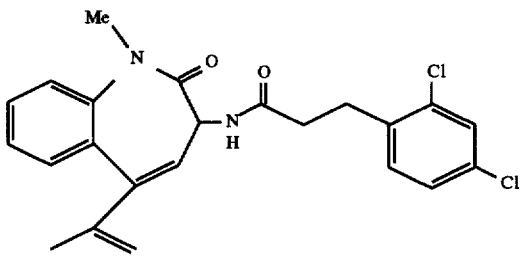

3-(2,4-Dichloro-phenyl)-N-5-(propene-2-yl)-1-methyl-2-oxo-2,3-dihydro-1H-benzo[b]azepin-3-propanamide

Step A

To a stirring solution of 3-(2,4-Dichloro-phenyl)-N-(1-methyl-2,5-dioxo-2,3,4,5-tetrahydro-1H-benzo[b]azepin-3-yl)-propionamide (7.1 mmol, 2.88 g) in 58 ml THF cooled in an ice bath was added the LDA (9.9 mmol, 5.0 ml of a 2M heptane/THF/ethylbenzene soln) dropwise and the solution stirred for 5 min. To this was added N-phenyltrifluoromethylsulfonimide (9.9 mmol, 3.54 g) and the reaction stirred in an ice bath for 1 h. The reaction was diluted with 200 ml H$_2$O and extracted with 2×100 ml EtOAc. The combined organics were dried with brine and Na$_2$SO$_4$ and evaporated under vacuum to a pale yellow solid. $^1$H NMR (300 MHz, CDCl$_3$) δ7.72–6.99 (m, 8H), 5.80 (d, J=4.9 Hz, 1H), 4.44 (t, J=5.6 Hz, 1H), 3.44 (s, 3H), 3.05 (t, J=7.6 Hz, 2H), 2.61 (t, J=7.6 Hz, 2H).

Step B

To a stirring solution of 2-bromopropene (6.5 mmol, 0.78 g, 0.58 ml) in 8 ml THF cooled to −78° C. was added tert-butyllithium (13.0 mmol, 7.6 ml of a 1.7M pentane solution) dropwise. This was stirred 10 min, trimethyl borate (8.45 mmol, 0.88 g, 0.96 ml) was added and the reaction allowed to warm to rt. Concentration of this solution was calculated to be 0.41M.

To a stirring solution of trifluoromethane sulfonic acid 3-[3-(2,4-dichlorophenyl)-propionylamino]-1-methyl-2-oxo-2,3-dihydro-1H-benzo[b]azepin-5-yl ester (1.3 mmol, 0.70 g) in 25 ml DME was added the Na$_2$CO$_3$ (2.6 mmol, 1.3 ml of a 2M aqueous solution), Pd[PPh$_3$]$_4$ (0.13 mmol,0.15), and LiCl (3.9 mmol, 0.16 g). To this was added 9.6 ml of the above boronate solution and the reaction heated to reflux for 2h. The reaction was cooled to rt, diluted with 200 ml saturated NaHCO$_3$ and extracted with 2×100 ml EtOAc. The combined organic layers were dried with Na$_2$SO$_4$ and evaporated under vacuum. The residue was chromatographed over silica, eluting with 25% EtOAc:Hex. Collected pure fractions, evaporated under vacuum, crystallized from Et$_2$O to give 160 mg of a white solid. mp 159°–161° C.

$^1$H NMR (300 MHz, CDCl$_3$) δ7.51–6.94 (m, 8H), 5.60 (d, J=5.4 Hz, 1H), 5.17 (s, 1H), 5.00 (s, 1H), 4.51 (t, J=5.9 Hz, 1H), 3.42 (s, 3H), 3.06 (t, J=7.3 Hz, 2H), 2.60 (t, J=7.3 Hz, 2H). Anal. Calcd for C$_{23}$H$_{22}$Cl$_2$N$_2$O$_2$.0.25 H$_2$O: C, 63.68; H, 5.23; N, 6.46. Found: C, 63.65; H, 5.03; N, 6.34.

EXAMPLE 16

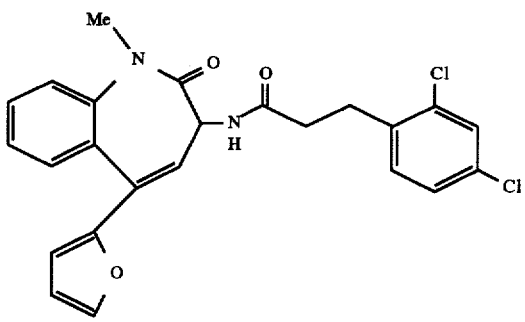

3-(2,4Dichloro-phenyl-5–2-furyl)-1-methyl-2-oxo-2,3-dihydro-1H-benzo[b]azepin-3-yl]propanamide

Step A

To a stirring solution of 3-(2,4-Dichloro-phenyl)-N-(1-methyl-2,5-dioxo-2,3,4,5-tetrahydro-1H-benzo[b]azepin-3-yl)-propionamide (7.1 mmol, 2.88 g) in 58 ml THF cooled in an ice bath was added the LDA (9.9 mmol, 5.0 ml of a 2M heptane/THF/ethylbenzene soln) dropwise and the solution stirred for 5 min. To this was added N-phenyltrifluoromethylsulfonimide (9.9 mmol, 3.54 g) and the reaction stirred in an ice bath for 1 h. The reaction was diluted with 200 ml H$_2$O and extracted with 2×100 ml EtOAc. The combined organics were dried with brine and Na$_2$SO$_4$ and evaporated under vacuum to a pale yellow solid. $^1$H NMR (300 MHz, CDCl$_3$) δ7.72–6.99 (m, 8H), 5.80 (d, J=4.9 Hz, 1H), 4.44 (t, J=5.6 Hz, 1H), 3.44 (s, 3H), 3.05 (t, J=7.6 Hz, 2H), 2.61 (t, J=7.6 Hz, 2H).

Step B

To a stirring solution of furan (2.8 mmol, 0.20 ml) in 2.0 ml THF cooled to −78° C. was added butyllithium (3.64 mmol, 1.46 ml of a 2.5M hexane solution) dropwise and the reaction stirred for 10 min. Trimethyl borate (3.64 mmol, 0.37 g, 0.41 ml) was then added and the reaction allowed to warm to rt. The solution was calculated to be 0.7M.

To a stirring solution of trifluoromethane sulfonic acid 3[3-(2,4-dichlorophenyl)-propionylamino]-1-methyl-2-oxo-2,3-dihydro-1H-benzo[b]azepin-5-yl ester (0.56 mmol, 0.3 g) in 10.5 ml DME was added the Na$_2$CO$_3$ (1.12 mmol, 0.56 ml of a 2M aqueous solution), Pd[PPh$_3$]$_4$ (0.28 mmol, 64.7 mg), and LiCl (1.68 mmol, 71.2 mg). The above boronate solution (1.4 mmol, 2.0 ml) was then added and the reaction heated to reflux for 2h. The reaction was allowed to cool to rt, diluted with 100 ml H$_2$O, and extracted with 2×50 ml EtOAc. The combined organics were dried with brine, Na$_2$SO$_4$ and evaporated under vacuum. The residue was chromatographed over silica, eluting with 25% to 50% EtOAc:Hex. Collected pure fractions, evaporated under vacuum, crystallized from Et$_2$O to give 68.0 mg of a light beige solid. mp 120°–124° C. $^1$HNMR. (300 MHz, CDCl$_3$) δ7.68–7.18 (m, 8H), 7.00–6.97 (m, 1H), 6.43–6.40 (m, 1H), 6.3–6.30 (m, 1H), 6.04 (d, J=5.9 Hz, 1H), 4.62 (t, J=6.1 Hz, 1H), 3.43 (s, 1H), 3.08 (t, J=7.6 Hz, 2H), 2.62 (t, J=7.6 Hz, 2H). Anal. Calcd for C$_{24}$H$_{20}$Cl$_2$N$_2$O$_3$.0.30 H$_2$O: C, 62.57; H, 4.51; N, 6.08. Found: C, 62.59; H, 4.21; N, 6.20.

EXAMPLE 17

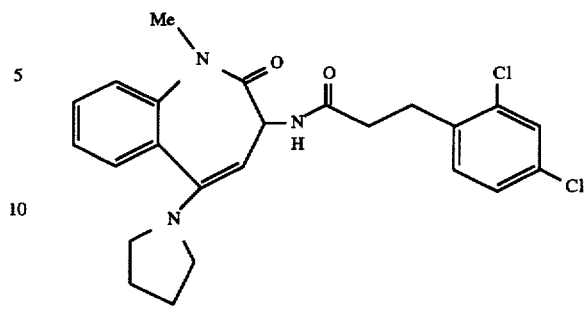

N-(1-methyl-5-pyrrolidinyl-2-oxo-2,3,4,5-tetrahydro-benzo[b]azepin-3-yl)-3-(2,4-dichlorophenyl)propionamide A solution of N-(1-methyl-2,5-dioxo-3,4-dihydro-1H-benzo[b]azepin-3-yl)-3-(2,4-dichlorophenyl)-propionamide (500 mg 1.2 mmole) and pyrrolidine (180 mg, 2.5 mmole) in methanol (50 mL) was treated with acetic acid (125 mg) and sodium cyanoborohydride (157 mg, 2.5 mmole) and stirred at room temperature for two days. The reaction was diluted with 200 ml saturated NaHCO$_3$ and extracted with 3×100 ml EtOAc. The combined organic layers were dried with MgSO$_4$ and evaporated at reduced pressure. The residue was chromatographed over silica, eluting with 2% MeOH chloroform to give two isomers. Each isomer was converted into the hydrochloride salt by treatment with excess ethanolic HCl.

Isomer A: 130 mg, mp 160°–163° C., Anal. Calcd for C$_{24}$H$_{27}$Cl$_2$N$_3$O$_2$.0.20 H$_2$O.0.2 IPA: C, 56.07; H, 6.05; N, 7.98. Found: C, 55.66; H, 5.99; N, 7.90.

Isomer B: 111 mg, mp 250°–252° C., Anal. Calcd for C$_{24}$H$_{27}$Cl$_2$N$_3$O$_2$.0.25 H$_2$O: C, 57.49; H, 5.73; N, 8.38. Found: C, 57.43; H, 5.70; N, 8.54.

EXAMPLE 18

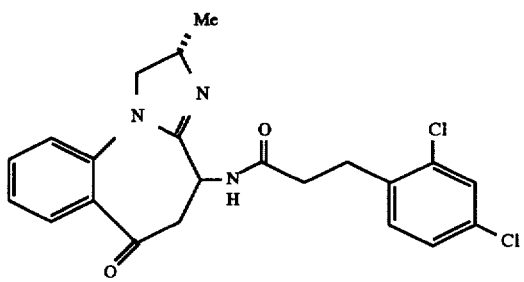

2-(S)-N-(1,2-dihydro-2-methyl-4H-imidazo[1,2-a]-6-oxobenzazepin-4-yl)-3-(2,4-dichlorophenyl)propanamide Step A:
3-tertbutyloxycarbonylamino-2,3,4,5-tetrahydro-2-thio-5-oxo-benzo[b]azepine To a stirring solution of 3-tertbutyloxycarbonylamino-2,3,4,5-tetrahydro-2,5-dioxobenzo[b]azepine (1.6 g, 5.5 mole) in THF (50 mL) was added Lawesson's reagent (2,4-bis(4-methoxy-phenyl)-1,3-dithia-2,4-diphosphetane-2,4-disulfide) (1.6 g, 4.1 mmole). The reaction was warmed gently and stirred at 60° C. for one hour. The reaction was cooled to room temperature and concentrated at reduced pressure. The residue was crystallized from methanol and the solid collected to give the product. 1.1 g $^1$H NMR (300 Mz, CDCl$_3$) δ9.52 (s, 1H), 7.83 (app, d, J=7 Hz, 1H), 7.59 (app, t, J=7 Hz, 1H), 7.38 (app, t, J=7 Hz, 1H), 7.03 (app d, J=7 Hz, 1H), 6.14 (d, J=5 Hz, 1H), 5.03 (m, 1H), 3.30 (d, J=3, 19 Hz, 1H), 3.02 (d, J=7, 19 Hz, 1H), 1.44 (s, 9H).

31

Step B:

1,2-dihydro-2-methyl-4-(tertbutyloxycarbonylamino)-4H-imidazo[1,2-a]-6-oxobenzazepine To a stirring solution of the thioamide from step A (3-tertbutyloxycarbonylamino-2,3,4,5-tetrahydro-2-thio-5-oxo-benzo[b]-azepine (612 mg, 2 mmole) was added (S)-2-aminopropanol (750 mg, 10 mmole), and mercury (II) chloride (541 mg, 2 mmole). The reaction was stirred at room temperature for 15 minutes, filtered and concentrated at reduced pressure. The residue was dissolved in ethyl acetate (200 mL) and washed with saturated sodium bicarbonate (100 mL). The organic layer was dried over anhydrous magnesium sulfate, filtered and concentrated. The residue was then chromatographed on silica gel eluting with 1.5%–5% methanol/-chloroform to give 502 mg of the intermediate hydroxyethyl amidine. The material thus obtained was dissolved in methylene chloride (20 mL) and treated with methanesulfonyl chloride (165 mg, 1.44 mmole) and Hunig's base (204 mg, 1.58 mmole). The reaction was stirred at room temperature for 15 minutes and then poured into saturated sodium bicarbonate (100 mL). The aqueous mixture was extracted with ethyl acetate (3×100 mL). The combined organics were dried over anhydrous magnesium sulfate, filtered, and concentrated at reduced pressure. The residue was then chromatographed on silica gel eluting with 2% methanol/chloroform. The pure fractions were combined and concentrated at reduced pressure. The residue was crystallized from ethyl acetate to give the product. 1 15 mg, mp 178°–181° C.

Anal. Calcd for $C_{18}H_{23}N_3O_2$: C, 65.63; H, 7.04; N, 12.76. Found: C, 65.38; H, 7.04; N, 12.54.

Step C:

2-(S)-N-(1,2-dihydro-2-methyl-4H-imidazo[1,2-a]-6-oxobenzazepin-4-yl)-3-(2,4-dichlorophenylopropanamide A solution of 1,2-dihydro-2-methyl-4-(tertbutyloxycarbonylamino)-4H-imidazo[1,2-a]-6-oxobenzazepine (760 mg, 2.3 mmole) ethyl acetate (100 was treated with excess HCl gas until all of the starting material had been consumed. The reaction was concentrated at reduced pressure and the material thus obtained was dissolved in DMF and treated with EDC (0.47 g, 2.76 mmole), HOBT (0.37 g, 2.76 mmole), 2,4-dichlorophenyl propionic acid (0.6 g, 2.76 mmole), and triethylamine (0.23 g, 2.3 mmole). The reaction was stirred at room temperature for 30 minutes and then poured into saturated sodium bicarbonate (400 mL). The aqueous mixture was extracted with ethyl acetate (3×100 mL). The combined organics were dried over anhydrous magnesium sulfate, filtered and concentrated at reduced pressure. The residue was then chromatographed with 1.5% methanol/chloroform to give the product (590 mg) as a mixture of isomers. The isomers were separated by chromatography on silica eluting with ethyl acetate.

Isomer A crystallized from ethylacetate/Hexane. Isomer B was converted into the hydrochloride salt and freeze dried.

Isomer A: mp 134°–136° C., Anal. Calcd for $C_{22}H_{21}Cl_2N_3O_2$: C, 62.25; H, 5.36; N, 9.39. Found: C, 62.04; H, 5.51; N, 9.06.

Isomer B: Anal Calcd for $C_{22}H_{21}Cl_2N_3O_2 \cdot HCl$: C, 53.60; H, 5.09; N, 8.53. Found: C, 53.56; H, 4.98; N, 8.19.

32

EXAMPLE 19

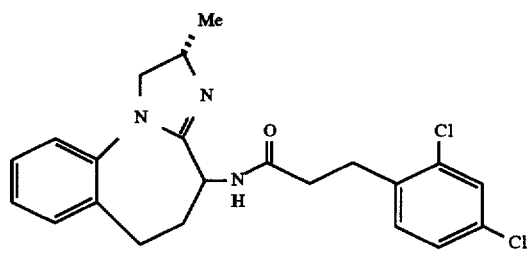

2-(S)-N-(1,2,5,6-tetrahydro-2-methyl-4H-imidazo[1,2-a]benzazepin-4-yl)-3-(2,4-dichlorophenyl)propanamide Step A 3-benzyloxyoxycarbonylamino-2,3,4,5-tetrahydro-2-thiobenzo[b]azepine To a stirring solution of of 3-benzyloxycarbonylamino-2,3,4,5-tetrahydro-2-oxobenzo[b]azepine (3.04 g, 0.98 mmole) in THF (100 mL) was added Lawesson's reagent (2,4-bis(4-methoxyphenyl)-1,3-dithia-2,4-diphosphetane-2,4-disulfide) (3 g, 0.75 mmole). The reaction was warmed gently and stirred at 60° C. for one hour. The reaction was cooled to room temperature and concentrated in vacuo. The residue was crystallized from methanol and the solid collected to give the product (2.3 g).

$^1$H NMR (CDCl$_3$) δ9.5 (s, 1H), 7.40–7.20 (m, 9H), 6.15 (d, J=7 Hz), 5.05 (app s, 2 H), 4.45 (m, 1H), 2.95–2.6 (m, 3H), 2.13–2.00 (m, 1H).

Step B 1,2-dihydro-2-methyl-4-(benzyloxycarbonylamino)-4H-imidazol[1,2-a]-benzazepine To a stirring solution of the thioamide from step A (3-benzyloxycarbonyiamino-2,3,4,5-tetrahydro-2-thiobenzo[b]azepine (980 mg, 3 mmole) was added (S)-2-aminopropanol (1.12 g, 15 mmole), and mercury (II) chloride (950 mg, 3.5 mmole). The reaction was stirred at room temperature for 15 minutes, heated to 60° C. for 1 hour, filtered and diluted with ethyl acetate (300 mL). The ethyl acetate solution was washed with saturated sodium bicarbonate (50 mL) and then brine (50 mL). The organic layer was dried over anhydrous magnesium sulfate, filtered and concentrated. The residue was dissolved in methylene chloride (75 mL) and treated with methanesulfonyl chloride (445 mg, 3.84 mmole) and Hunig's base (956 mg, 7.4 mmole). The reaction was stirred at room temperature for 15 minutes, diluted with ethyl acetate (300 mL), and then poured into saturated sodium bicarbonate (200 mL). The layers were separated and the aqueous mixture was extracted with ethyl acetate (2×100 mL). The combined organics were dried over anhydrous magnesium sulfate, filtered, and concentrated at reduced pressure. The residue was then chromatographed on silica gel eluting with 2%–3% methanol/chloroform. The residue was crystallized from ether to give the product. (850 mg) as a mixture of diastereomers. mp 140°–142° C.

Anal. Calcd for $C_{21}H_{23}N_3O_2$: C, 71.81; H, 6.66; N, 11.96. Found: C, 71.76; H, 6.63; N, 11.86.

Step C:

2-(S)-N-(1,2,5,6-tetrahydro-2-methyl-4H-imidazo[,1,2-a]benzazepin-4-yl)-3-(2,4-dichlorophenylopropanamide.

A solution of 1,2-dihydro-2-methyl-4-(benzyloxycarbonylamino)-4H-imidazo[1,2-a]benzazepine (458 mg, 1.31 mmole) in methylene chloride (4 mL) was treated with excess HBr in acetic acid (5 mL of 30% solution) until all of the starting material had been consumed. The reaction was diluted with ether (100 mL) and the solvent decanted. The solid was washed with three additional 50 mL portions of ether and the solid dried at reduced pressure. The material thus obtained was dissolved in DMF and treated with EDC (0.259 g, 1.35 mmole) HOBT (0.182 g, 1.35 mmole), and 2,4-dichlorophenyl propionic acid (0.296 g, 1.35 mmole). The reaction was stirred at room temperature for 90 minutes and then poured into saturated sodium bicarbonate (100 mL). The aqueous mixture was extracted with ethyl acetate (3×100 mL). The combined organics were dried over anhydrous magnesium sulfate, filtered, and concentrated at reduced pressure. The residue was then chromatographed on silica gel eluting with 2%–4% methanol/chloroform to give the product (151 mg) as a mixture of isomers. The mixture was converted into the hydrochloride salt and freeze dried.

Anal. Calcd for $C_{22}H_{23}Cl_2N_3O,1.8\ H_2O$: C, 54.45; H, 5.73; N, 8.66. Found: C, 54.49; H, 5.54; N, 8.58.

What is claimed is:

1. A compound of the structural formulae I and II

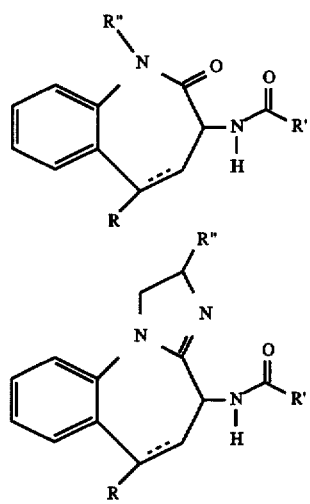

or a pharmaceutically acceptable salt, hydrate or crystal form thereof wherein:

R is a straight or branched alkyl of $C_1$ to $C_6$, arylalkyl, aryl, heteroaryl, O-alkyl, O-acyl, carboxylic acid, aldehyde, ketone, ester or amide: R' is a straight or branched alkyl of $C_1$ to $C_6$, arylalkyl, aryl, N-aryl, O-alkyl, O-aryl and R" is a straight or branched alkyl or aryl.

2. The compound of claim 1 selected from the group consisting of these depicted in the following table:

3. The compound of claim 1 selected from the group consisting of these depicted in the following table:

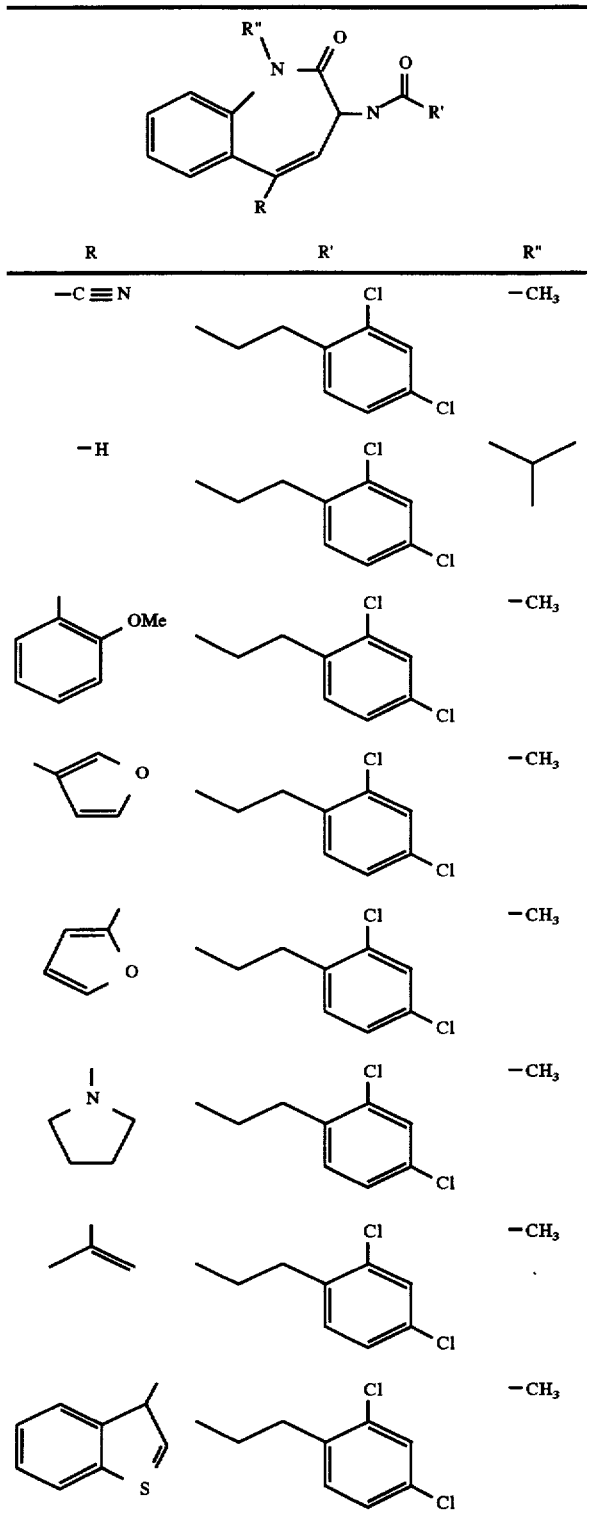

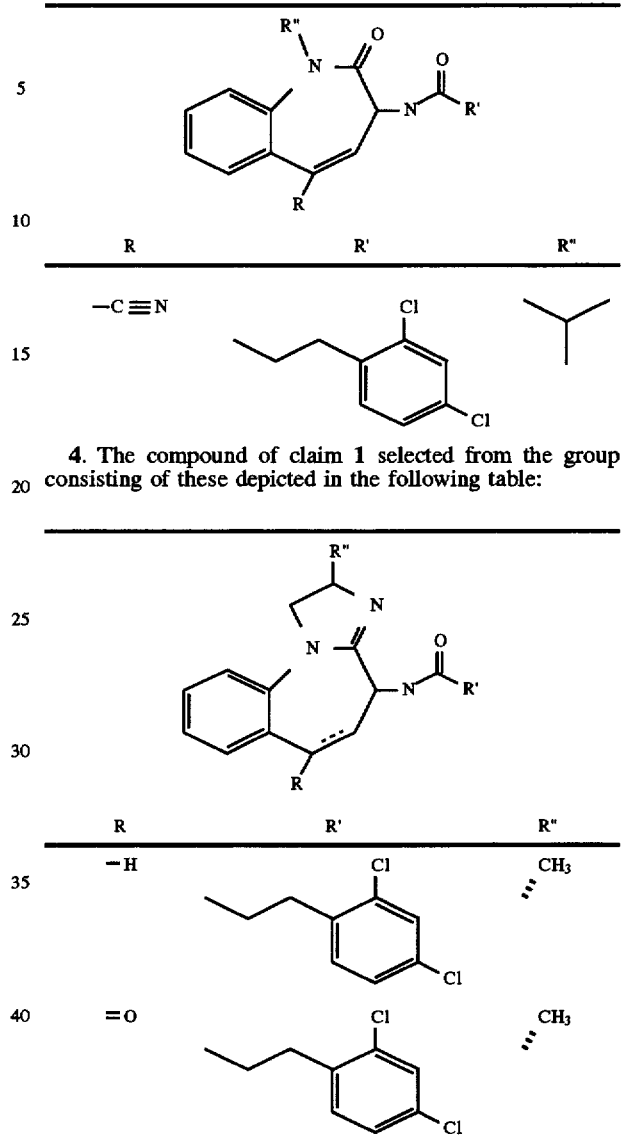

4. The compound of claim 1 selected from the group consisting of these depicted in the following table:

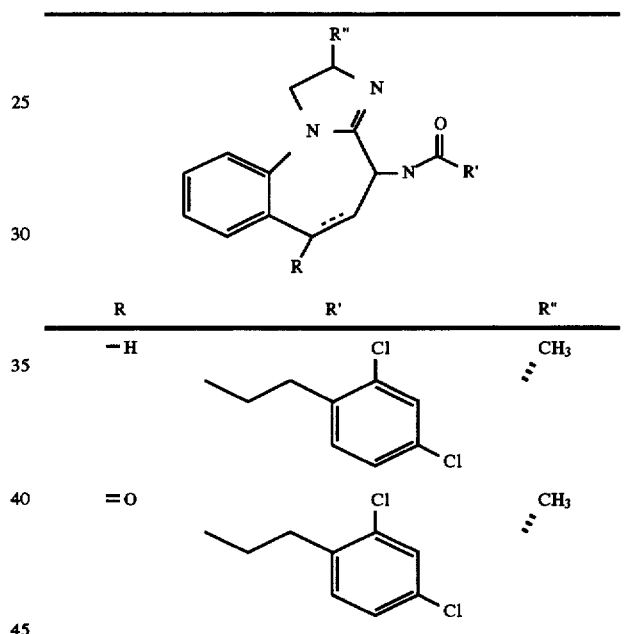

5. A pharmaceutical formulation comprising a pharmaceutically acceptable carrier and a therapeutically effective amount of the compound of claim 1 or a pharmaceutically acceptable salt, crystal form or hydrate thereof.

6. The pharmaceutical formulation of claim 5 comprising in addition another antiarrhythmic agent or other cardiovascular agent.

7. A method of preventing or treating arrhythmia which comprises the administration to a patient in need of such treatment of an antiarrhythmically effective amount of the compound of claim 1.

8. The method of claim 7 comprising the concomitant administration of another antiarrhythmic agent or other cardiovascular agent.

* * * * *